(12) United States Patent
Hunter

(10) Patent No.: US 9,220,739 B1
(45) Date of Patent: Dec. 29, 2015

(54) ALL NATURAL BODY POWDER THAT BALANCES YOUR PH AND ELIMINATES, BACTERIA, FUNGUS, MICROBES AND ANY BODY ODOR, INCLUDING ODOR PASSED ONTO ARTICLES OF CLOTHING OR SHOES

(71) Applicant: Shaun Hunter, Ferndale, WA (US)

(72) Inventor: Shaun Hunter, Ferndale, WA (US)

( * ) Notice: Subject to any disclaimer, the term of this patent is extended or adjusted under 35 U.S.C. 154(b) by 149 days.

(21) Appl. No.: 13/972,264

(22) Filed: Nov. 5, 2013

(51) Int. Cl.
*A61K 33/22* (2006.01)
*A61K 36/53* (2006.01)
*A61K 36/534* (2006.01)
*A61K 36/61* (2006.01)
*A61L 9/01* (2006.01)
*A61L 2/23* (2006.01)

(52) U.S. Cl.
CPC ............... *A61K 36/61* (2013.01); *A61K 33/22* (2013.01); *A61K 36/53* (2013.01); *A61K 36/534* (2013.01); *A61L 2/23* (2013.01); *A61L 9/01* (2013.01); *A61L 2202/20* (2013.01)

(58) Field of Classification Search
CPC ......... A61L 2/23; A61L 2202/20; A61L 9/01; A61K 33/22; A61K 36/53; A61K 36/534; A61K 36/61
See application file for complete search history.

(56) References Cited

U.S. PATENT DOCUMENTS 6,579,543 B1 * 6/2003 McClung ...................... 424/728

FOREIGN PATENT DOCUMENTS

CN 102362849 A * 2/2012

* cited by examiner

*Primary Examiner* — Abigail Fisher
*Assistant Examiner* — Daniel L Branson

(57) ABSTRACT

An all-natural, multi-purpose body powder comprised of Boric Acid, Organic Lavender, Tea Tree, *Eucalyptus* and Peppermint. The ratios of Boric Acid to Organic Lavender and Tea Tree are 288:1. The ratios of Boric Acid to Organic *Eucalyptus* and Peppermint are 1728:1. All of said ingredients create an environment that bacteria cannot grow in, wherein body, foot and shoe odor is prevented.

3 Claims, No Drawings

ALL NATURAL BODY POWDER THAT BALANCES YOUR PH AND ELIMINATES, BACTERIA, FUNGUS, MICROBES AND ANY BODY ODOR, INCLUDING ODOR PASSED ONTO ARTICLES OF CLOTHING OR SHOES

BACKGROUND OF THE INVENTION

The present invention relates to topical powders suitable for use on mammalian skin applied to feet, in socks, shoes and protective sport pads.

Prior all-natural body powders, specifically foot powders, use cornstarch, arrowroot or talc. While these powders help with moisture absorption, they lack in properties important to preventing odor. The said powders create problems with residue build-up in shoes. Other fragrances may be added to cover up odor.

SUMMARY OF THE INVENTION

An all-natural, multi-purpose body powder comprised of Boric Acid, Organic Lavender, Tea Tree, *Eucalyptus* and Peppermint. The properties of the body powder alone and with said essential oils are anti-bacterial, anti-microbial, anti-fungal, antiseptic, anti-inflammatory and useful for reducing and/or preventing body odor and moisture. The prior problems and inadequacies of foot powders have been solved through using Boric Acid. Not only does Boric Acid absorb moisture, prevent residue build-up, and contain anti-bacterial, anti-fungal and antiseptic properties, it also has a similar acidic value to table salt which balances the PH on your body and in your shoes. These properties combined provide a base powder that creates an environment bacteria will not grow in and far exceeds the capabilities of prior body, foot and shoe deodorizers.

DETAILED DESCRIPTION OF THE INVENTION

An all-natural, multi-purpose body powder comprised of Boric Acid ($H_3BO_3$), Organic Lavender (*Lavandula angustifolia*), Tea Tree (*Melaleuca alternifolia*), Eucalyptus (*Eucalyptus globulus*) and Peppermint (*Mentha arvensis*). The all-natural body powder combined with said essential oils are capable of treating body odor due to its acidic value, moisture absorption, anti-bacterial, anti-fungal, anti-microbial and antiseptic and anti-inflammatory properties. All of said properties create an environment that bacteria will not grow in. The said ingredients are combined and mixed in a commercial size mixer. The ratios of Boric Acid to Organic Lavender and Tea Tree are 288:1. The ratios of Boric Acid to Organic *Eucalyptus* and Peppermint are 1728:1. The body powder is packaged in powder dispensing containers. The all-natural body powder relates to reducing and/or preventing body odor and moisture, specifically to the feet and shoes. To treat body odors, the body powder may be applied directly to feet, inside shoes, socks, protective sport pads, etc. on a daily basis. This daily regimen may continue one, two or three weeks depending on the severity of the odor. After the odor has been treated, the regimen may be continued every other day or twice per week to control odor dependent on activity levels and frequency of use of said objects.

I claim:

1. An all-natural shoe deodorizer consisting of boric acid and four organic essential oils whereby body odor is eliminated from footwear through direct application inside said footwear.

2. The shoe deodorizer of claim 1 wherein said essential oils are 1 ounce of organic lavender oil, 1 ounce of tea tree oil, 0.17 ounces of *eucalyptus* oil and 0.17 ounces of peppermint oil per 288 ounces of boric acid.

3. A method of deodorizing footwear comprising dispensing the deodorizer of claim 1 directly into said footwear.

\* \* \* \* \*